United States Patent

West, Jr. et al.

[11] Patent Number: 6,149,646
[45] Date of Patent: Nov. 21, 2000

[54] MONOPOLAR TISSUE ABLATOR

[75] Inventors: Hugh S. West, Jr., Salt Lake City, Utah; Robert A. Van Wyk, Largo, Fla.

[73] Assignee: Linvatec Corporation, Largo, Fla.

[21] Appl. No.: 09/243,060

[22] Filed: Feb. 2, 1999

[51] Int. Cl.⁷ .................................................. A61B 18/18
[52] U.S. Cl. ................................. 606/41; 606/49; 606/45
[58] Field of Search .................................. 606/41, 42, 45, 606/48–50

[56] References Cited

U.S. PATENT DOCUMENTS

| | | |
|---|---|---|
| 2,275,167 | 3/1942 | Bierman . |
| 2,888,928 | 6/1959 | Seiger . |
| 3,825,004 | 7/1974 | Durden, III . |
| 3,826,263 | 7/1974 | Cage et al. . |
| 3,828,780 | 8/1974 | Morrison, Jr. . |
| 3,902,494 | 9/1975 | Haberien et al. . |
| 3,920,021 | 11/1975 | Hiltebrandt . |
| 3,970,088 | 7/1976 | Morrison . |
| 3,974,833 | 8/1976 | Durden, III . |
| 3,987,795 | 10/1976 | Morrison . |
| 4,043,342 | 8/1977 | Morrison, Jr. . |
| 4,074,718 | 2/1978 | Morrison, Jr. . |
| 4,161,950 | 7/1979 | Doss et al. . |
| 4,202,337 | 5/1980 | Hren et al. . |
| 4,228,800 | 10/1980 | Degler, Jr. et al. . |
| 4,232,676 | 11/1980 | Herczog . |
| 4,347,842 | 9/1982 | Beale . |
| 4,674,499 | 6/1987 | Pao ........................................... 606/50 |
| 4,882,777 | 11/1989 | Narula . |
| 4,920,980 | 5/1990 | Jackowski . |
| 5,089,002 | 2/1992 | Kirwan, Jr. . |
| 5,281,216 | 1/1994 | Klicek ....................................... 606/42 |
| 5,366,443 | 11/1994 | Eggers et al. . |
| 5,382,247 | 1/1995 | Cimino et al. ........................... 606/33 |
| 5,571,101 | 11/1996 | Ellman et al. . |
| 5,683,366 | 11/1997 | Eggers et al. . |
| 5,697,281 | 12/1997 | Eggers et al. . |
| 5,697,536 | 12/1997 | Eggers et al. . |
| 5,697,882 | 12/1997 | Eggers et al. . |
| 5,697,909 | 12/1997 | Eggers et al. . |
| 5,702,387 | 12/1997 | Arts et al. ................................. 606/45 |
| 5,800,431 | 9/1998 | Brown . |
| 5,814,043 | 9/1998 | Shapeton ................................... 606/48 |
| 5,843,019 | 12/1998 | Eggers et al. . |
| 5,938,658 | 8/1999 | Tu ............................................ 606/41 |
| 6,004,317 | 12/1999 | Speiser ..................................... 606/41 |

FOREIGN PATENT DOCUMENTS

| | | |
|---|---|---|
| 295 03 626 U | 3/1995 | Germany . |
| WO 98/09575 | 3/1998 | WIPO . |
| WO 99/44523 | 10/1999 | WIPO . |

OTHER PUBLICATIONS

ESA Electrosurgical Arthroscopy Electrodes, Linvatec Product Catalog, pp. G–1 Through G–5, 1998.

*Primary Examiner*—Michael Peffley
*Attorney, Agent, or Firm*—Gene Warzecha

[57] ABSTRACT

A monopolar electrode for use with a standard electrosurgical pencil and generator suitable for performing tissue ablation at relatively low power levels. The electrode has a cylindrical rim at its distal tip, the exposed conductive area of the cylindrical rim being minimized to create high powered densities sufficient for tissue ablation. The distal end of the electrode is surrounded by a ceramic insulating sleeve and an annular insulating gap is interposed between the electrode and the ceramic sleeve. A tubular polymeric insulating sleeve is applied to the outer surface of the electrode and to the outer surface of the proximal end of the ceramic sleeve.

9 Claims, 4 Drawing Sheets

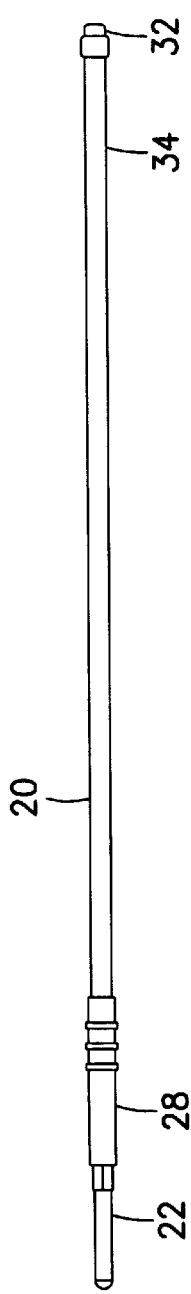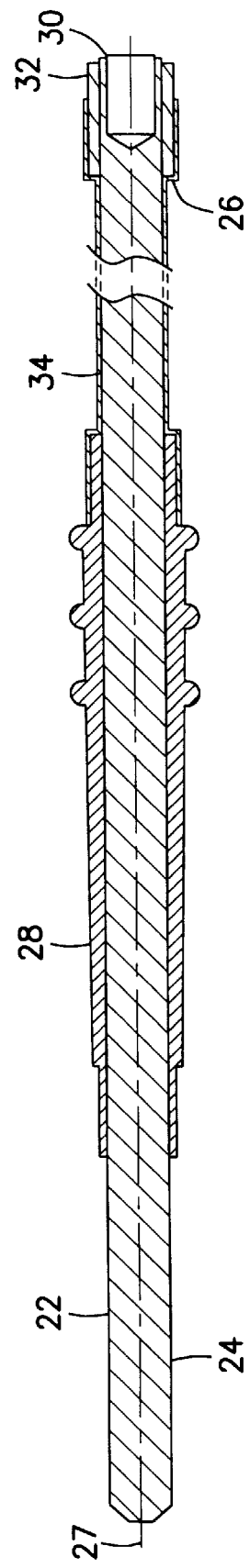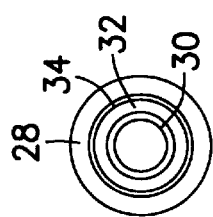

MONOPOLAR TISSUE ABLATOR

BACKGROUND OF THE INVENTION

1. Field of the Invention

The invention relates to the ablation of tissue during electrosurgical procedures. More particularly, the invention relates to tissue ablation by a monopolar electrosurgical device in a fluid environment during arthroscopic procedures.

2. Description of the Prior Art

Electrosurgical procedures are commonly performed in either a monopolar mode, using a probe having an active electrode placed adjacent tissue to be operated upon, with a return or common electrode placed externally on the patient's body, or a bipolar mode where both active and return electrodes are on the same probe. The procedures are being used to cut or coagulate tissue, these different functions accomplished by applying a different energy waveform and/or power level to the electrodes. Recently, bipolar electrosurgical devices have been developed for endoscopic tissue ablation at surgical sites filled with a conductive fluid rather than simply cutting or coagulation. Such new devices require special, dedicated and costly electrosurgical generators, new bipolar electrode designs and high power levels. The term "ablation" in the context of a surgical procedure is generally defined as the removal of tissue by vaporization. Ablation has the connotation of removing a relatively large volume of tissue. It can be stated that since ablation is the removal of tissue by high-density electrical discharge in a conductive fluid environment, ablation of a sort occurs from the edges of all electrosurgical electrodes used in a cutting mode. This effect, which is independent of whether the return path is provided by a conventional return pad (i.e. monopolar) or a return electrode immersed in the conductive fluid filled space (i.e. bipolar), is related to the volumetric ablation which is the subject of this invention. However, the ablative properties of the invention will be understood to be quite different from known devices.

It is well known to surgeons that for a given electrode design, higher power values give increased rates of tissue removal because the volume of tissue removed (during cutting, for example) is dependent on the power density at the active electrode. This applies to monopolar and bipolar devices. However, the power density required for tissue ablation has not generally been available over large enough surfaces in known monopolar electrodes and that is why surgeons desiring to perform electrosurgical volumetric ablation have had to use the aforementioned bipolar ablation systems.

Power density on the surface of a monopolar electrode is somewhat dependent on the conductivity of tissues or fluids in contact with the electrode. The conductive fluids used in electrosurgery are highly conductive and produce non-uniform current density at the electrode surface. Maximizing this power density over large enough surfaces facilitates tissue ablation, and the invention facilitates the proper power density over large enough surfaces at power levels lower than the aforementioned bipolar tissue ablation devices.

For an electrosurgical instrument working in a space filled with conductive fluid, such as during an arthroscopic procedure, current density is higher at the edges of the electrode than on its broader or flatter surfaces. When sufficient power is supplied, the current density at the edge of an electrode in this environment is sufficient to raise the temperature of the fluid thereby making it more conductive. The increased current flow due to this increased conductivity further raises the fluid temperature, which increases the conductivity, which increases the current flow, etc. This continues until the fluid at the electrode edge begins to form a gas phase due to boiling and a luminous discharge becomes visible due to localized arcing. It is believed that the high current density discharge and intense heat at the electrode edge actually perform the ablation. Similarly, bringing the edge of the instrument into contact or sufficiently close proximity with tissue will facilitate initiation of discharge from the edge of the electrode nearest the tissue. If sufficient power is supplied after such high-density discharge is initiated, the instrument can be withdrawn slightly from the tissue while maintaining the high-density discharge at the electrode edge. This phenomenon is well known to surgeons using conventional monopolar electrosurgical instruments.

Although all electrodes used in a cutting mode in a field filled with conductive fluid produce ablation at their edges, not all electrode shapes are equally useful for the removal of relatively large volumes of tissue by ablation. For example, conventional blade-like electrodes are poorly suited for the bulk ablation of tissue due to the small amount of edge area able to produce high density discharge. Similarly, solid cylindrical electrodes also have a small amount of edge area compared to non-edge area. The inherent inefficiency of these shapes necessitates very high power levels relative to the surface area. The efficiency of an electrode for bulk ablation of tissue may be defined as the amount of energy dissipated as high-density ablative discharge divided by the total energy dissipated by the device. Because the electrode is immersed in a conductive fluid, energy will flow from all uninsulated surfaces in contact with the fluid, although energy flowing from non-edge areas will be at a lower density level and will, therefore, dissipate in the fluid with no desirable effect. This low density discharge can be minimized by insulating the non-edge surfaces from the conducting fluid and/or selecting electrode shapes which minimize non-edge surface areas.

The invention with its tubular structure has been discovered suitable for large volume tissue ablation in a monopolar mode at lower power levels and with conventional electrosurgical generators, thus enabling electrosurgical ablation with much simpler and less costly monopolar systems.

While other monopolar suction electrodes having a tubular cross-section are known and commonly used in nonarthroscopic surgery, they are suitable only for cutting or coagulation and will not ablate if placed in a fluid-filled arthroscopic environment. Their inability to ablate is the result of the manner in which they are insulated. That is, they generally have a layer of relatively thin polymeric insulation extending to within a specified relatively large distance of the electrode distal tip. The specified distance is such that a large area of the electrode (typically approximately 4 mm in diameter and 4 mm in length) is exposed so as to allow coagulation through contact between the tubular electrode's external circumferential surface and the tissue in the non-arthroscopic environment for which they are designed. Such a cautery would be ineffective in a saline environment due to the large uninsulated surface area as virtually all of the current would diffuse into the saline with no ablative clinical effect.

It is accordingly an object of this invention to produce an electrosurgical tissue ablator suitable for use with conventional electrosurgical generators in a monopolar mode.

It is also an object of this invention to produce a monopolar tissue ablator capable of ablating relatively large volumes of tissue at relatively low power levels.

It is also an object of this invention to produce a monopolar electrode capable of producing high power density levels sufficient for tissue ablation while being driven by relatively low power levels, preferably less than approximately 50 watts.

It is also an object of this invention to produce a monopolar electrode capable of producing tissue ablation within a surgical field filled with conductive fluid.

SUMMARY OF THE INVENTION

These and other objects are achieved by the preferred embodiment disclosed herein which employs a solid electrically conductive electrode having a tubular distal end with a cylindrical rim. The distal end is insulated by a tubular ceramic insulator and an outer polymeric insulating sleeve to prevent conduction of current from most of the exterior circumferential surface of the tubular electrode. The ceramic insulator extends to within a critical distance of the distal tip of the metal electrode so that a large fraction of the power supplied to the electrode is conducted into the ambient saline with sufficient current density to cause tissue ablation at low power levels. The ceramic insulator may extend to the distal face of the tubular electrode section or even slightly beyond, however, the ablative effect of electrodes insulated in this manner is less than that of electrodes on which a small portion of the electrode's circumferential surface is exposed to the saline. If excessive area of the external circumferential surface is exposed, higher power levels are required to initiate an ablative discharge as a larger portion of the power is diffused into the saline as low density current producing no desirable clinical effect.

BRIEF DESCRIPTION OF THE DRAWINGS

FIG. 2 is a side elevation view, in approximate actual size, of the monopolar electrode constructed in accordance with the principles of this invention.

FIG. 3 is an enlarged cross-sectional view of FIG. 2.

FIG. 4 is a right end view of FIG. 3.

DESCRIPTION OF THE PREFERRED EMBODIMENT

Figure 1:
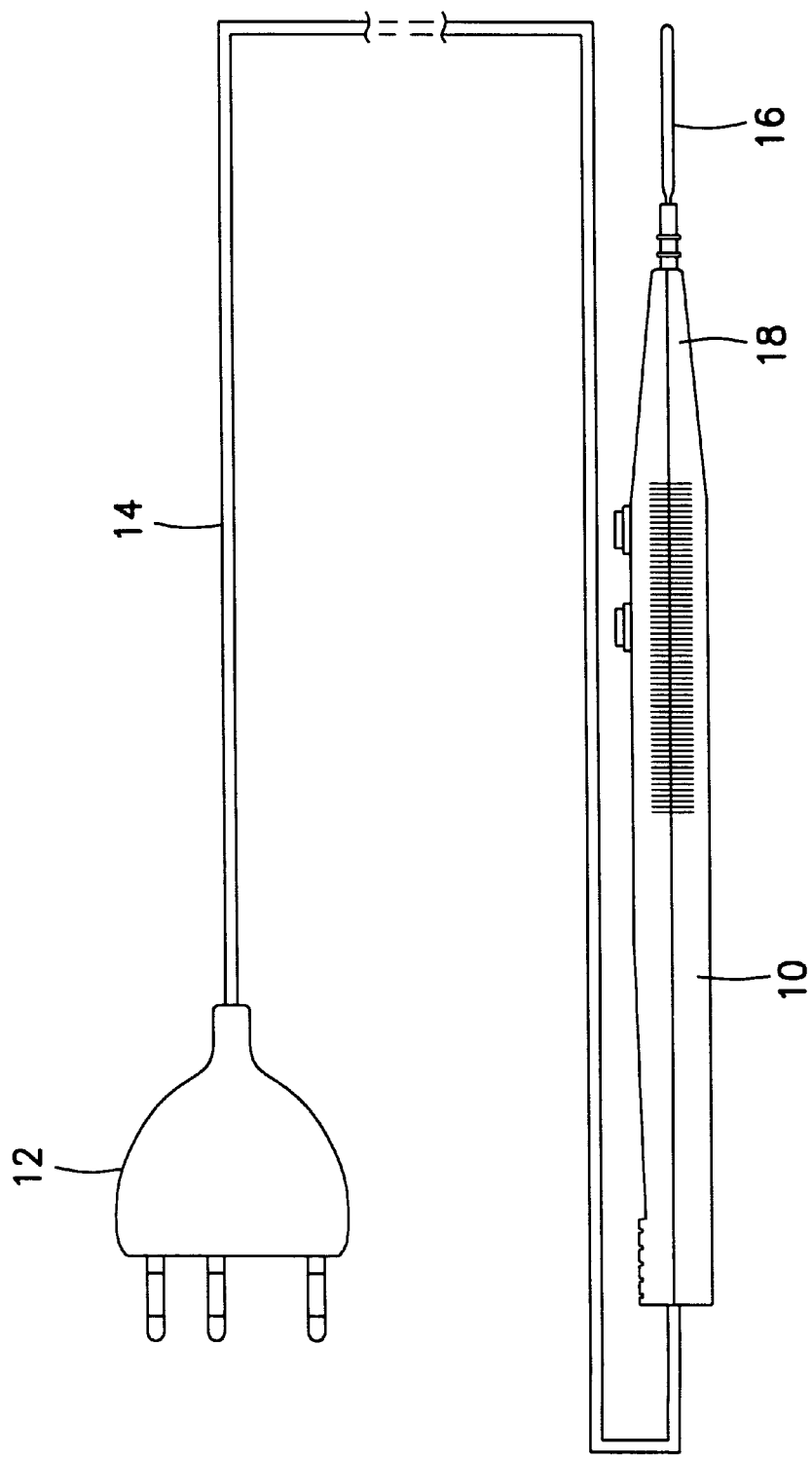
FIG. 1 is a diagrammatic view of a prior art electrosurgical pencil connected at one end to an electrode and at the other end to a plug for connection to an electrosurgical generator.

Referring now to FIG. 1, there is shown a conventional monopolar electrosurgical pencil 10 connected to a plug 12 via a power cord 14. Pencil 10 is a conventional unit which is designed to be plugged into a conventional electrosurgical generator (not shown) and is adapted to receive a variety of electrodes 16 in its distal end 18.

An ablation electrode 20 constructed in accordance with the principles of this invention is shown at approximately actual size in FIG. 2 and enlarged in FIG. 3. Electrode 20 comprises an electrically conductive cylindrical rod 22 having a proximal end 24, a distal end 26 and an axis 27. Rod 22 is secured to and extends through a conventional polymeric hub 28 adapted to facilitate connecting the electrode to pencil 10. The distal end 26 is provided with an annular, distally facing, cylindrical rim 30 in order to enable the ablation of tissue in a monopolar mode at low power levels. The cylindrical, tubular shape of the electrode enables the minimization of the conductive area of the electrode while also enabling 360° omni-directional use in the plane of the electrode rim. Unlike a knife or blade edge which can only be used in limited directions because the power density at the electrode surface facing the direction of motion varies depending upon the orientation of the device, the cylindrical rim can provide the same power density over 360° about its axis. The tubular electrode need not be cylindrical but could have any cross-sectional shape so as to allow the fabrication of specialized shapes for specific applications.

The tubular electrode shape enables ablation at low power levels and is, therefore, more efficient than known solid cylinder electrodes since the ratio of edge area to non-edge area is greater. Production of the tubular shaped tip and rim necessitates production of a recess 40. However, if desired, all conduction from the inner surfaces bordering recess 40 can be prevented by placing an insulator in the bore of the tube, thereby enhancing performance through the elimination of power loss due to low density discharge from these inner surfaces. While an option this is not absolutely necessary for satisfactory performance. In like manner, insulating a substantial portion of the external circumferential surface of the rod also enhances the efficiency of the tubular electrode.

Figure 6:
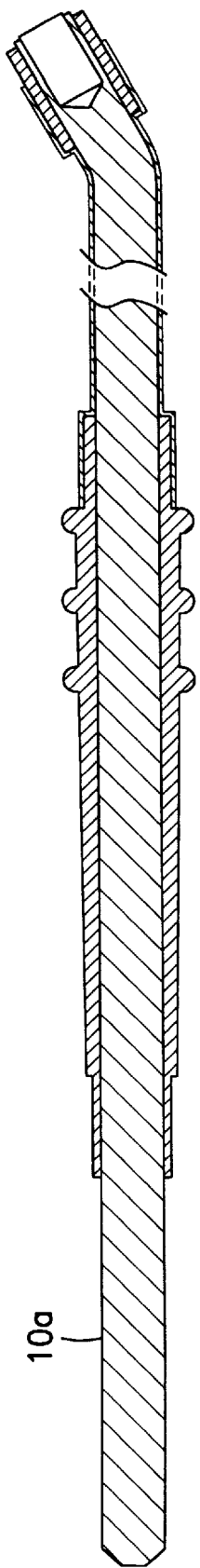
FIG. 6 is an enlarged cross-sectional view of alternate embodiment of the electrode shown in FIG. 3.
Figure 7:
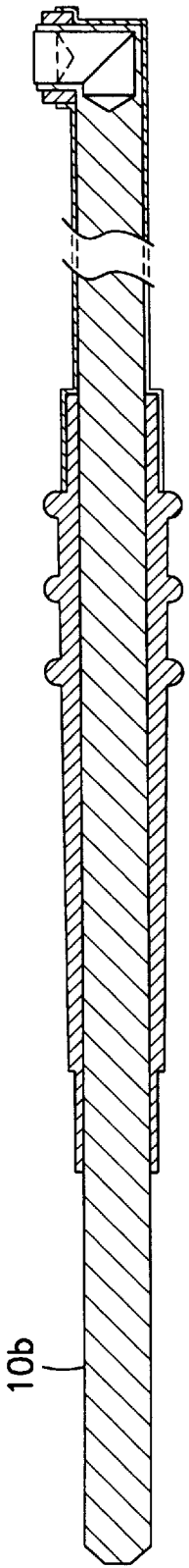
FIG. 7 is an enlarged cross-sectional view of another alternate embodiment of the electrode shown in FIG. 3.

Distal end 26 is surrounded by a coaxial ceramic insulator sleeve 32 and a polymeric insulator sleeve 34. Sleeve 34 extends longitudinally along electrode 10 covering the external surface of rod 22 and the adjacent distal and proximal exterior surfaces of hub 28 and sleeve 32, respectively. Ceramic sleeve 32 is a high temperature insulator which serves to electrically insulate the cylindrical exterior surface of distal end 26 from any conductive fluid or tissue. Sleeve 32 must be thick enough and must extend proximally a predetermined distance sufficient to dissipate enough heat to enable it to continue to insulate the distal end of the electrode without cracking. Any breakage of the ceramic might not only compromise patient safety, but could destroy the ablative action by decreasing power density at the electrode rim below the requisite threshold. The ceramic sleeve also sufficiently insulates the polymeric sleeve thermally to maintain the integrity of the latter at the high temperatures produced at the electrode tip during use. This also maintains the energy density required for ablation throughout the duration of the surgical procedure. The length L2 (FIG. 5) of the ceramic sleeve is limited only by the desirability of bending the distal tip 26 for certain (endoscopic or arthroscopic) surgical procedures. An electrode with a bent tip (such as shown in FIGS. 6 and 7) must pass through a cannula (having, for example, a 5.5 mm internal diameter) so the ceramic sleeve must be short enough to enable such a bend while large enough and long enough to provide sufficient insulation. Sleeve 34 is preferably sufficiently pliable to enable it to insulate rod 22 even if it is bent intentionally or unintentionally during use. While the rod is solid stainless steel it may be bent for certain procedures. Also, even if not intentionally bent, sometimes surgeons may inadvertently stress the electrode by using it to push or pry elements during a procedure.

Ceramic material has been chosen for the insulator sleeve 32 due to its ability to withstand the high temperatures produced at the electrode distal tip during ablation. It is noted, however, that not all ceramics are able to withstand the high temperatures and thermal gradients present at the distal tip of the electrode. The thermal conductivity and thermal diffusivity of the ceramic have a significant effect on its suitability and performance, more so than absolute strength. The ceramic insulator used in the preferred embodiment is made from an extruded alumina ($Al_2O_3$) based material AD-998 Round Single Bore Tubing available from Coors Ceramics Company of Golden, Colo. (Partially stabilized zirconia material, though stronger and tougher for some applications, is unacceptable because of spalling and gross cracking due to thermal effects.)

In the preferred embodiment, sleeve 34 is made of polyolefin shrink tubing, although other higher temperature polymeric materials may be used as required. For example, liquid materials could be used to coat the electrode or granular, particulate materials could be baked on. The primary requirement is that the material produce a sleeve having sufficient dielectric strength and suitable flexibility and thermal properties.

Figure 5:
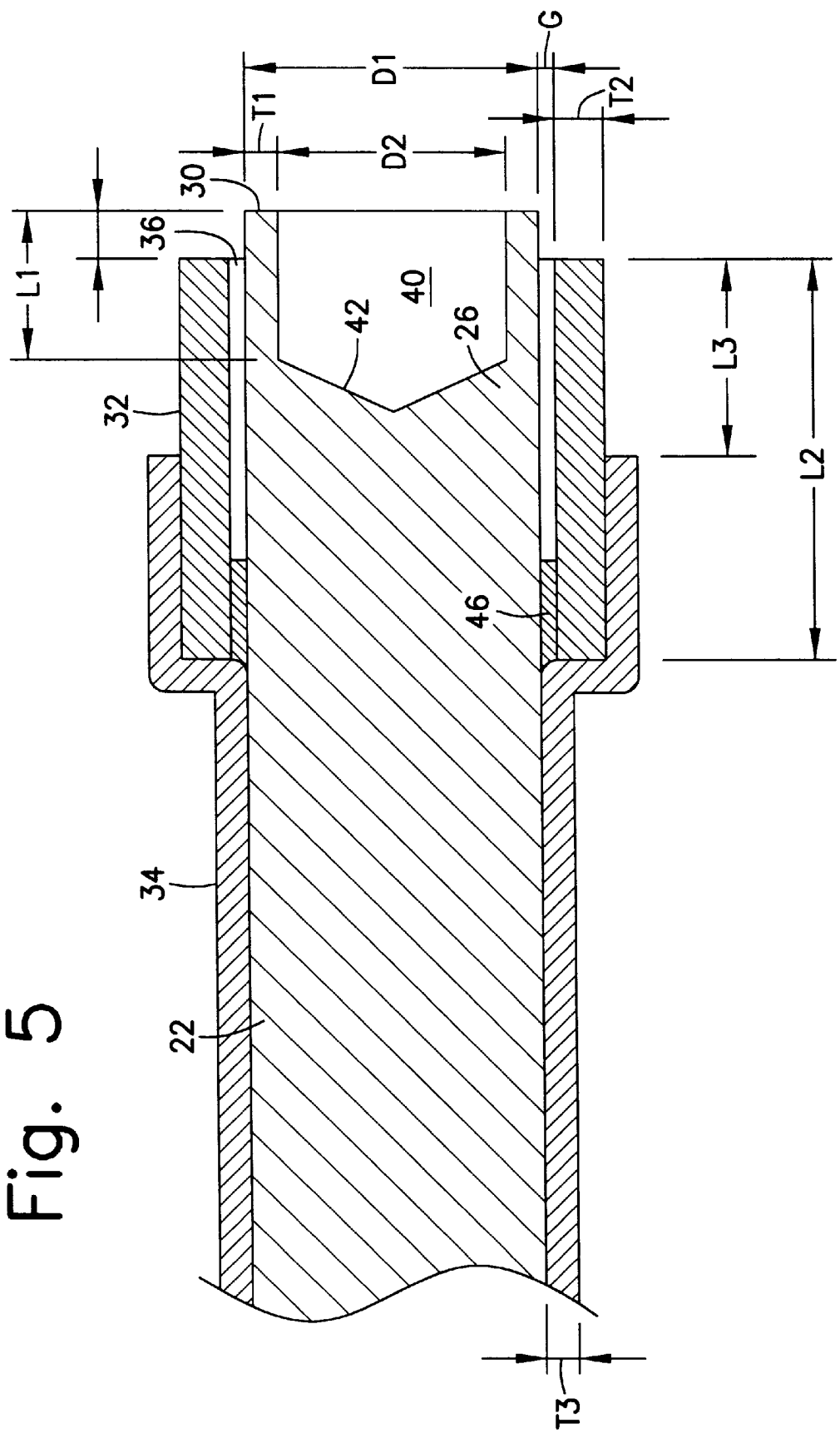
FIG. 5 is an enlarged cross-sectional view of the distal tip of the electrode shown in FIGS. 2 and 3.

As best seen in the enlarged view of FIG. 5, annular electrode rim 30 and ceramic insulator 32 are separated by an annular gap 36 in order to allow for thermal expansion of the distal end 26 of rod 22. During use, the distal tip of the electrode experiences a significant temperature rise. Due to the difference in the coefficients of thermal expansion of the metal electrode and the tubular ceramic insulator, a certain minimum radial clearance preferably exists between the electrode rod and the insulator. Insufficient clearance will result in cracking of the insulator as the electrode heats up and expands during ablation. A similar gap is not necessary near polymeric sleeve 34 since it is relatively flexible and the temperature rise of the electrode rod in this area is significantly less than at the distal tip 30.

In the preferred embodiment, an adhesive is used to attach the ceramic insulator to the electrode rod. The adhesive must be applied in such a manner that it does not fill gap 36 in the distal region which experiences the greatest temperature increases. This is accomplished by applying the adhesive (a suitable biocompatible high temperature epoxy), to the extreme proximal portion of the ceramic insulator only, and ensuring that the adhesive has sufficient viscosity (prior to curing) to prevent migration of the adhesive into the distal portion of the gap. The presence of adhesive in the distal portion of the electrode/insulator gap may cause cracking of the ceramic insulator during use as the electrode distal end expands due to heating.

An axially aligned cylindrical recess 40 is provided in the distally facing surface of rod 22 in order to minimize the exposed conducting electrode surface to increase the power density on the annular electrode rim.

In a preferred embodiment, electrode 10 is made of stainless steel approximately 130 mm long and having a diameter of D1 of 2.4 mm (0.094 inches). The diameter D2 of recess 40 is 2.1 mm (0.082 inches) and the thickness T1 of rim 30 is therefore 0.15 mm (0.006 inches). Recess 40 has a depth L1 of 1 mm (0.04 inches) and its blind end may have a variety of shapes, the shape shown being produced by a drill point for ease of fabrication. Ceramic sleeve 32 has a thickness T2 of 0.3 mm (0.012 inches) and a length L2 of 3.0 mm (0.12 inches). Gap 36 has an annular thickness G of 0.04 mm (0.0015 inches) and is as long as sleeve 32 except for epoxy 46 situated between rod 22 and sleeve 32 at the proximal most side of gap 36. Polymeric insulating sleeve 34 (polyolefin) has a thickness T3 of 0.25 mm (0.01 inches) and is spaced from the distal most end of ceramic sleeve 32 by a distance L3 of 0.13 mm (0.05 inches). While an electrode constructed with these dimensions has been found to ablate tissue at input power levels on the order of 30–50 watts, it will be understood that satisfactory ablation may occur at lower power levels with dimensional changes in the electrode. That is, power required is proportional to the exposed electrode area. Additionally, some users may prefer to operate at power levels greater than 50 watts for certain tissue. In view of the above, the intended power range for the invention is deemed to be a range on the order of 0–100 watts, preferably 30–50 watts.

As shown in FIGS. 6 and 7 the distal end of rod 22 may be bent relative to the axis of the rod at 30° or 90°, respectively, or any other suitable angle to produce alternate electrode embodiments 10a and 10b.

While the embodiments disclosed herein utilize an annular insulating gap, the purpose of this gap is to prevent cracking of the rigid, inflexible ceramic insulating sleeve. If insulating materials become available which can perform the function of the ceramic sleeve while enabling the sleeve to expand in response to thermal expansion of the electrode tip, such an annular gap may be unnecessary.

It will be understood by those skilled in the art that numerous improvements and modifications may be made to the preferred embodiment of the invention disclosed herein without departing from the spirit and scope thereof.

What is claimed is:

1. A monopolar electrode for use with an electrosurgical pencil connected to an electrosurgical generator, said electrode comprising:
    a single electrically conductive electrode rod having a distal end and a proximal end with an axis, said proximal end adapted to be connected to said electrosurgical pencil, said distal end terminating in a conducting annular rim;
    a first insulating tubular sleeve coaxially situated about said rod at said distal end; and
    a polymeric second insulating tubular sleeve coaxially situated about a predetermined proximal portion of said first insulating sleeve and said electrode rod.

2. A monopolar electrode according to claim 1 wherein said annular rim is unitarily formed with said electrode rod.

3. A monopolar electrode according to claim 1 wherein said annular rim comprises a distally facing surface and a laterally facing surface extending a predetermined distance from said distally facing surface.

4. A monopolar electrode according to claim 1 wherein said polymeric second insulating sleeve is flexible enough to insulate said electrode even if said electrode rod is bent.

5. A monopolar electrode according to claim 1 wherein said first insulating tubular sleeve is ceramic.

6. A monopolar electrode according to claim 1 wherein said distal end of said electrode rod has an axis that is coaxially aligned with said axis of said proximal end.

7. A monopolar electrode for use with an electrosurgical pencil connected to an electrosurgical generator, said electrode comprising:
    an electrically conductive electrode rod having a distal end and a proximal end with an axis, said proximal end adapted to be connected to said electrosurgical pencil, said distal end terminating in a conducting annular rim;
    a first insulating tubular sleeve coaxially situated about said rod at said distal end;
    a polymeric second insulating tubular sleeve coaxially situated about a predetermined proximal portion of said first insulating sleeve and said electrode rod; and
    an annular insulation gap interposed between said distal end of said electrode rod and said first insulating sleeve, said gap having a predetermined axial length.

8. A monopolar electrode according to claim 7 wherein said first insulating tubular sleeve is secured to said distal end of said rod by an adhesive situated at the proximal-most end of said annular insulation gap.

9. A method of performing monopolar tissue ablation on a patient prepared for a monopolar surgical procedure comprising the steps of:

provideing a monopolar electrode for use with an electrosurgical pencil connected to an electrosurgical generator comprising:

an electrically conductive electrode rod having a distal end and a proximal end with an axis, said proximal end adapted to be connected to said electrosurgical pencil, said distal end terminating in a conducting annular rim;

a first insulating tubular sleeve coaxially situated about said rod at said distal end;

an annular insulation gap interposed between said distal end of said electrode rod and said first insulating sleeve, said gap having a predetermined axial length; and a polymeric second insulating tubular sleeve coaxially situated about a predetermined proximal portion of said first insulating sleeve and said electrode rod; and connecting said monopolar electrode to an electrosurgical generator and applying to said electrode an energy waveform having a power level of less than 100 watts.

* * * * *